(12) United States Patent
Gengler

(10) Patent No.: US 7,294,139 B1
(45) Date of Patent: Nov. 13, 2007

(54) CONTROLLED - MOTION ENDOSCOPIC GRASPING INSTRUMENT

(75) Inventor: Mark S. Gengler, Shelby, NC (US)

(73) Assignee: C.M. Wright, Inc., Shelby, NC (US)

( * ) Notice: Subject to any disclaimer, the term of this patent is extended or adjusted under 35 U.S.C. 154(b) by 851 days.

(21) Appl. No.: 10/206,530

(22) Filed: Jul. 26, 2002

(51) Int. Cl.
*A61B 17/00* (2006.01)
(52) U.S. Cl. ...................................... 606/206; 606/113
(58) Field of Classification Search .................. 606/51, 606/52, 106, 107, 113, 170, 205, 200; 623/1.11, 623/1.12
See application file for complete search history.

(56) References Cited

U.S. PATENT DOCUMENTS

| | | | | | |
|---|---|---|---|---|---|
| 4,198,960 | A | * | 4/1980 | Utsugi ........................... | 128/6 |
| 4,222,380 | A | * | 9/1980 | Terayama ..................... | 128/216 |
| 4,427,014 | A | | 1/1984 | Bel et al. ..................... | 128/751 |
| 4,467,802 | A | * | 8/1984 | Maslanka ..................... | 606/206 |
| 4,598,699 | A | * | 7/1986 | Garren et al. .................. | 128/4 |
| 5,052,402 | A | | 10/1991 | Bencini et al. .............. | 128/751 |
| 5,089,007 | A | | 2/1992 | Kirsch et al. ................ | 606/205 |
| 5,098,440 | A | * | 3/1992 | Hillstead ..................... | 606/108 |
| 5,122,147 | A | * | 6/1992 | Sewell ........................ | 606/110 |
| 5,171,233 | A | * | 12/1992 | Amplatz et al. ............. | 604/281 |
| 5,176,688 | A | * | 1/1993 | Narayan et al. ............. | 606/128 |
| 5,176,702 | A | * | 1/1993 | Bales et al. .................. | 606/205 |
| 5,250,056 | A | * | 10/1993 | Hasson ..................... | 606/151 |
| 5,336,227 | A | * | 8/1994 | Nakao et al. ................ | 606/114 |
| 5,376,094 | A | * | 12/1994 | Kline ........................ | 606/113 |
| 5,499,997 | A | * | 3/1996 | Sharpe et al. ............... | 606/206 |
| 5,638,827 | A | * | 6/1997 | Palmer et al. .............. | 600/564 |
| 5,645,075 | A | | 7/1997 | Palmer et al. .............. | 128/749 |
| 5,667,525 | A | * | 9/1997 | Ishibashi ..................... | 606/206 |
| 5,683,388 | A | * | 11/1997 | Slater ......................... | 606/51 |
| 5,706,824 | A | | 1/1998 | Whittier ..................... | 128/751 |
| 5,716,374 | A | | 2/1998 | Francese et al. ............ | 606/207 |
| 5,776,075 | A | * | 7/1998 | Palmer ....................... | 600/564 |
| 5,797,957 | A | * | 8/1998 | Palmer et al. .............. | 606/205 |
| 5,928,250 | A | * | 7/1999 | Koike et al. ................ | 606/139 |
| 5,944,728 | A | * | 8/1999 | Bates ......................... | 606/127 |
| 6,033,424 | A | | 3/2000 | Ouchi ........................ | 606/205 |
| 6,123,678 | A | | 9/2000 | Palmer et al. .............. | 600/567 |
| 6,149,607 | A | | 11/2000 | Simpson et al. ............ | 600/567 |
| 6,361,540 | B1 | * | 3/2002 | Gauderer et al. ........... | 606/106 |
| 6,375,661 | B2 | * | 4/2002 | Chu et al. ................... | 606/113 |
| 6,478,794 | B1 | * | 11/2002 | Trapp et al. ................. | 606/45 |
| 2001/0053923 | A1 | * | 12/2001 | Sato et al. ................... | 606/215 |

\* cited by examiner

*Primary Examiner*—Anhtuan T. Nguyen
*Assistant Examiner*—Elizabeth Houston
(74) *Attorney, Agent, or Firm*—Kennedy Covington Lobdell & Hickman, LLP

(57) ABSTRACT

An improved controlled-motion instrument is provided for grasping, holding or otherwise manipulating an object in operations such as endoscopic procedures. The instrument opens and closes jaws or other manipulation members by way of a longitudinally movable cam member, but maintains the longitudinal position of the manipulation members constant relative to the instrument's body regardless of opening and closing motion. The manipulation members thus have increased length-to-diameter ratio and column strength, and the cam provides positive lateral jaw support and stability during opening and closing. The movable cam member can also include other manipulation members thereon that work in conjunction with the longitudinally fixed manipulation members.

9 Claims, 10 Drawing Sheets

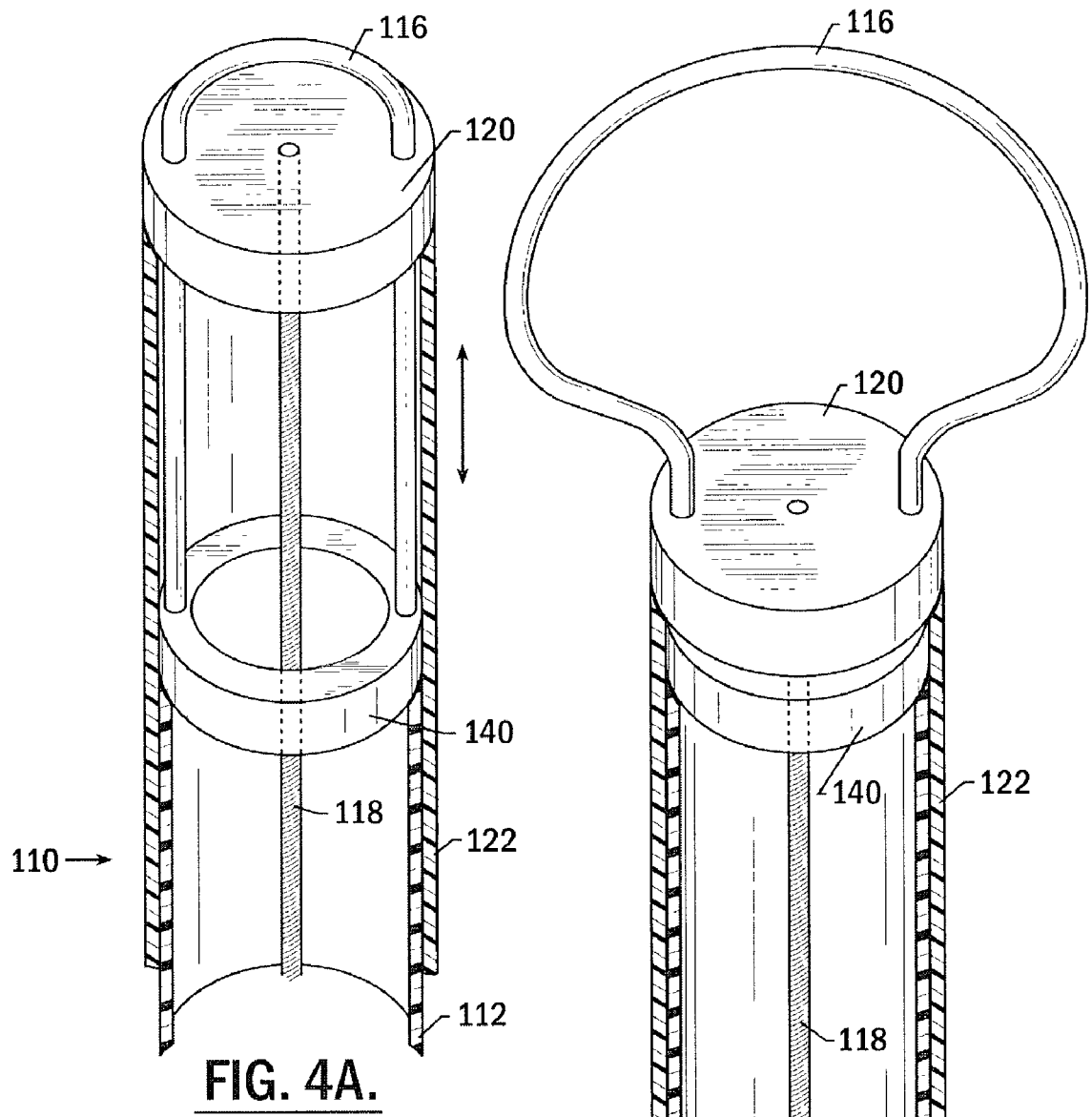

CONTROLLED - MOTION ENDOSCOPIC GRASPING INSTRUMENT

BACKGROUND AND SUMMARY OF THE INVENTION

The present invention relates generally to instruments for grasping, gripping or manipulating distant objects and more particularly to endoscopic instruments for performing such operations as part of a medical procedure.

Flexible forceps or other grasping instruments are frequently used in conjunction with flexible endoscopes or other visualization devices for retrieving or otherwise manipulating objects within a patient's body without the need for conventional surgical intervention and the attendant risk and resultant patient recovery. Conventional forceps or graspers of this type frequently include an elongated, tightly-wound spring-coil sheath or body having a "handle" or other such control assembly at a proximal end and a jaw assembly at a distal end, with the distal end being inserted through a body opening either separately or through an endoscope. The control assembly is typically a hand-operated push-pull mechanism that extends and retracts a control wire or thin cable through a longitudinally-extending lumen in the sheath or body. The control wire in such instruments is attached to pivoting thin wire jaws that are spring-biased laterally outwardly to open when they are extended longitudinally outwardly beyond the end of the sheath or body and to close when retracted longitudinally back within the sheath.

As a result, these prior art jaws move longitudinally relative to the instrument's sheath or body and move relative to the object to be grasped or manipulated, during opening and closing. This makes it difficult for the operator to accurately position and open and close the moving jaw assembly around the stationary object, especially in the very close quarters typically encountered in medical endoscopic procedures. These jaws can also thus move into and out of the focal range of the endoscope, thus further complicating the operator's ability to see and accurately maneuver them relative to the object. Furthermore, in order to be able to open wide enough to surround or enclose the object to be manipulated, the jaws in such prior art designs are necessarily inordinately long. Because these long jaws must also be very thin in order to allow the instrument to be inserted through small body openings, their length-to-diameter (L/D) ratio is high, often 100/1 or even higher. Thus the typically resilient jaws, which are laterally unrestrained and unsupported when extended to their open positions, often lack sufficient column strength or stiffness to prevent significant jaw deflection or displacement relative to the object, to prevent undesirable changes in jaw shape or geometry, or to avoid loss of accurate jaw positioning relative to the object. This often results in undue repeated maneuvering of the instrument to get it into proper position, repeated attempts to grasp and hold or otherwise manipulate an object, and the resultant trauma and damage to the surrounding tissue in medical endoscopic procedures.

The present invention seeks to overcome these and other disadvantages by providing an improved controlled-motion instrument for grasping, holding or otherwise manipulating an object in operations such as those performed in the course of endoscopic procedures. The present invention's instrument maintains the longitudinal position of its jaws or other manipulation members relative to the body of the instrument regardless of their opening and closing, has greatly improved jaw L/D ratio and column strength, provides greatly improved lateral jaw support and stability during opening and closing, and can include other instrument features in conjunction with a grasping function in order to eliminate or at least minimize the need for multiple or repeated instrument insertions in many procedures.

According to the present invention, an instrument for manipulating an object preferably includes a generally hollow elongated sheath or body, with a selectively operable "handle" or operating assembly generally adjacent one end and one or more jaws or other manipulation members generally adjacent an opposite end. It is important to note that the manipulation member or members are generally fixed, longitudinally, relative to the sheath and is preferably interconnected, directly or indirectly, with the sheath or body. The manipulation member or members are preferably resilient and at least partially deflectable in at least one non-longitudinal direction.

An elongated activation member extends generally longitudinally within the sheath or body for longitudinally movement therein. The activation member, which is preferably a wire or thin cable, can have a round, oval, rectangular, or other cross-sectional shapes that will occur to those skilled in the art. The activation member is interconnected adjacent one of its ends with the handle or operating assembly so as to be selectively moved longitudinally between a retracted position relative to the sheath and an extended position relative to the sheath when the manually operable handle or other operating assembly or mechanism is activated.

A cam member is fixed relative to the activation member, preferably adjacent its opposite end, for corresponding longitudinal movement therewith between retracted and extended positions. The longitudinally moveable cam member engages and forcibly deflects the longitudinally fixed manipulation members or jaws in at least one non-longitudinal direction in response to selective operation of the operating assembly. Thus the cam member forces the jaws or other manipulation members into engagement with the object even though they remain generally fixed relative to the sheath during such deflection, grasping, gripping or holding.

The longitudinally fixed manipulation member assembly can also include two or more thin wire jaws, each optionally having an inwardly or outwardly facing barb or other object-gripping discontinuity, and the jaws can be arranged to be opened or closed upon either extension or retraction of the activation and cam members. The longitudinally fixed manipulation member can alternately be in the form of a snare-type loop, of either a one-piece or multi-piece construction, and can be spread or contracted upon either extension or retraction of the activation and cam members. As a further alternate or optional embodiment, the manipulation member or assembly can have a "basket" type construction or configuration, with two or more arcuate or spiraling members, preferably laterally restrained relative to each other at their proximate or distal ends. When the cam member is extended or retracted, the basket-type members constrict or expand in order to be maneuvered to enclose and grip or grasp the object to be manipulated.

In any of the invention's arrangements, the individual single or multiple jaw or manipulation members can have virtually any cross-sectional shape, such as round or other arcuate shapes, or even rectangular or other polygonal shapes, in order to suit a particular application or to obtain certain desired directional deflection characteristics.

The cam member can be of a disk shape, a rectangular or other polygonal shape, a bead or sphere shape, or even a partially open cup-like shape, with or without recesses therein for receiving barbs or other discontinuities on retracted jaws. Preferably, the cam member has one or more openings extending generally longitudinally through it for slidably receiving a corresponding portion or portions of the manipulation member or members extending therethrough as the extending or retracting cam member forcibly engages the manipulation member or members. The preferred cam members also include outer sleeves that move with them and are long enough to slidably overlap the sheath during extension and retraction in order to minimize the potential for body tissue or other materials being introduced into the hollow sheath.

Optionally, the cam member can also include one or more secondary manipulation members or assemblies interconnected and moveable with the cam member separately and independently of the longitudinally fixed manipulation members. Such "cam-mounted" manipulation members can include a sharpened needle or probe, a knife blade, or a gripping discontinuity for example. Such secondary or supplemental manipulation members can be used in conjunction with the fixed manipulation members to grasp, grip, hold or even cut or sever the object to be manipulated or retrieved.

Also, in an alternate construction, more than one additional wire, cable or other member can be interconnected with the cam member to allow unequal forces to be exerted on different parts of the cam member and cause the cam member to turn or "steer" the sheath or body member along "non-straight-line "paths, such as those typically encountered in medical endoscopic procedures. This arrangement can be used even in instruments not having manipulation jaws, such as when an endoscope is inserted solely for visual observation purposes, for example.

Other objects, advantages and features of the present invention, in addition to those examples mentioned above, will become apparent from the following description and the appended claims, taken in conjunction with the accompanying drawings.

BRIEF DESCRIPTION OF THE DRAWINGS

FIGS. 4A and 4B are detailed partial cross-sectional views similar to those of FIGS. 3A and 3B, but illustrating an alternate longitudinally fixed manipulation member, in the form of a snare or loop, shown in its open and closed conditions, respectively.

DESCRIPTION OF THE PREFERRED EMBODIMENTS

Figure 1:
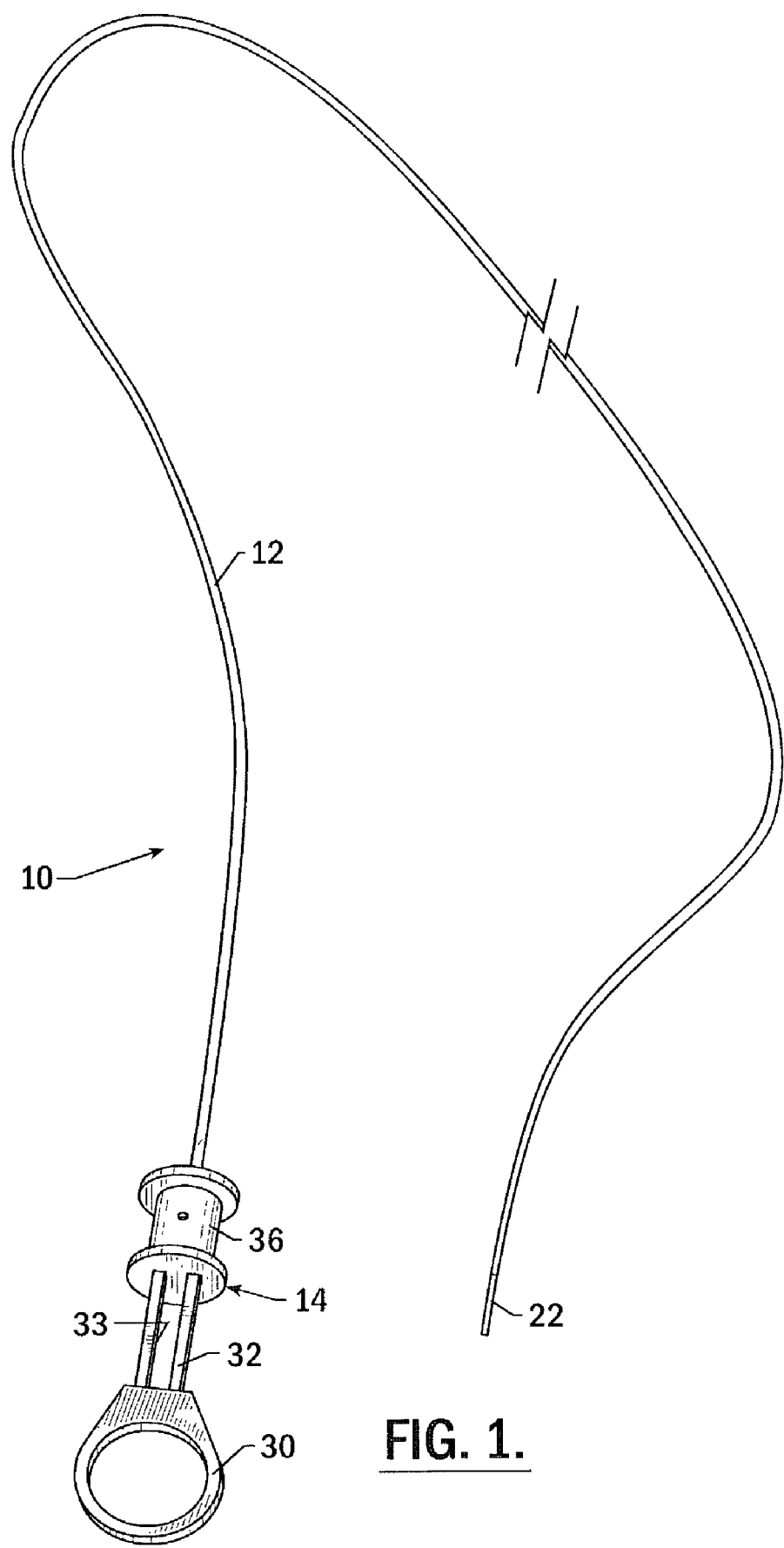
FIG. 1 is a perspective view of one exemplary preferred embodiment of a controlled-motion grasping instrument according to the present invention.

FIGS. 1 through 10 of the accompanying drawings depict various merely exemplary embodiments of controlled-motion grasper assemblies according to the present invention. Such illustrations are shown for purposes of illustration herein as being applicable in endoscopic instruments. One skilled in the art will readily recognize, however, that other embodiments according to the invention can also be employed and that the invention can be equally and advantageously used in other medical or non-medical grasping, gripping or holding applications.

Referring initially to FIGS. 1 through 3B, an exemplary endoscopic grasping instrument 10 includes a generally hollow, longitudinally elongated sheath or body 12 having a handle or other operating assembly 14 adjacent one end and generally wire-like jaws or manipulation members 16 adjacent its opposite end. In the illustrative form shown in the drawings, the handle 14 can have a "thumb" portion 30 having one or more slides or track portions 32 extending therefrom and spaced apart to from a slide opening 33 therebetween. A slide 34 (see FIG. 2C) is slidably received within the opening 33 and is moved therein by a "finger" portion through its interconnection by way of a fastener 38. As one skilled in the art will readily appreciate, it should be emphasized that other manually or non-manually actuatable operating assemblies can also be alternately employed.

A wire-like activation member or draw cable 18 slidably extends through the hollow sheath 12 and is interconnected at or adjacent one end with the exemplary slide 34 of the handle 14 and with a cam member 20 at or adjacent its opposite end. When the handle or other operating assembly 14 is activated, the cable 18 and the cam member 20 are extended or retraced relative to the hollow sheath 12. The movable cam member 20 extends and retracts longitudinally inwardly and outwardly along the longitudinally fixed jaws 16, which extend through openings in the cam member 20 and which remain fixedly interconnected with the sheath 14 (such as by way of an anchor ring 40 fixed to the distal end of the sheath 40) during such cam extension and retraction. However, because the longitudinally fixed jaws 16 are preferably resilient and biased generally laterally or radially outwardly, they open when the cam member 20 is retracted relative to the sheath 12 and are deflected toward their closed positions when the cam member 20 is extended.

Figure 2A:
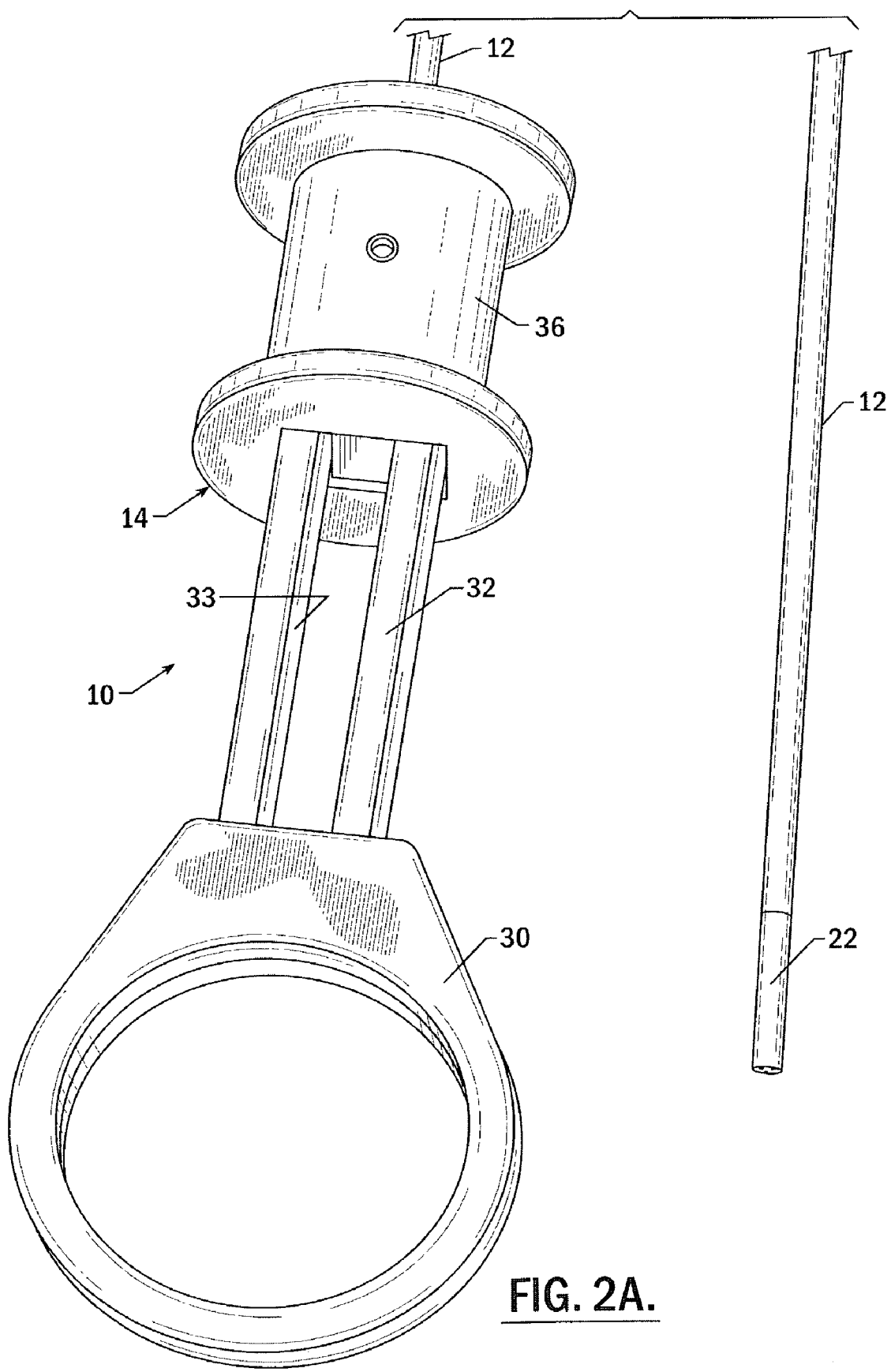
FIG. 2A is a perspective view similar to that of FIG. 1, but enlarged, with portions cut away, showing the instrument's cam member and outer sleeve fully extended to close the longitudinally fixed manipulation members.
Figure 2B:
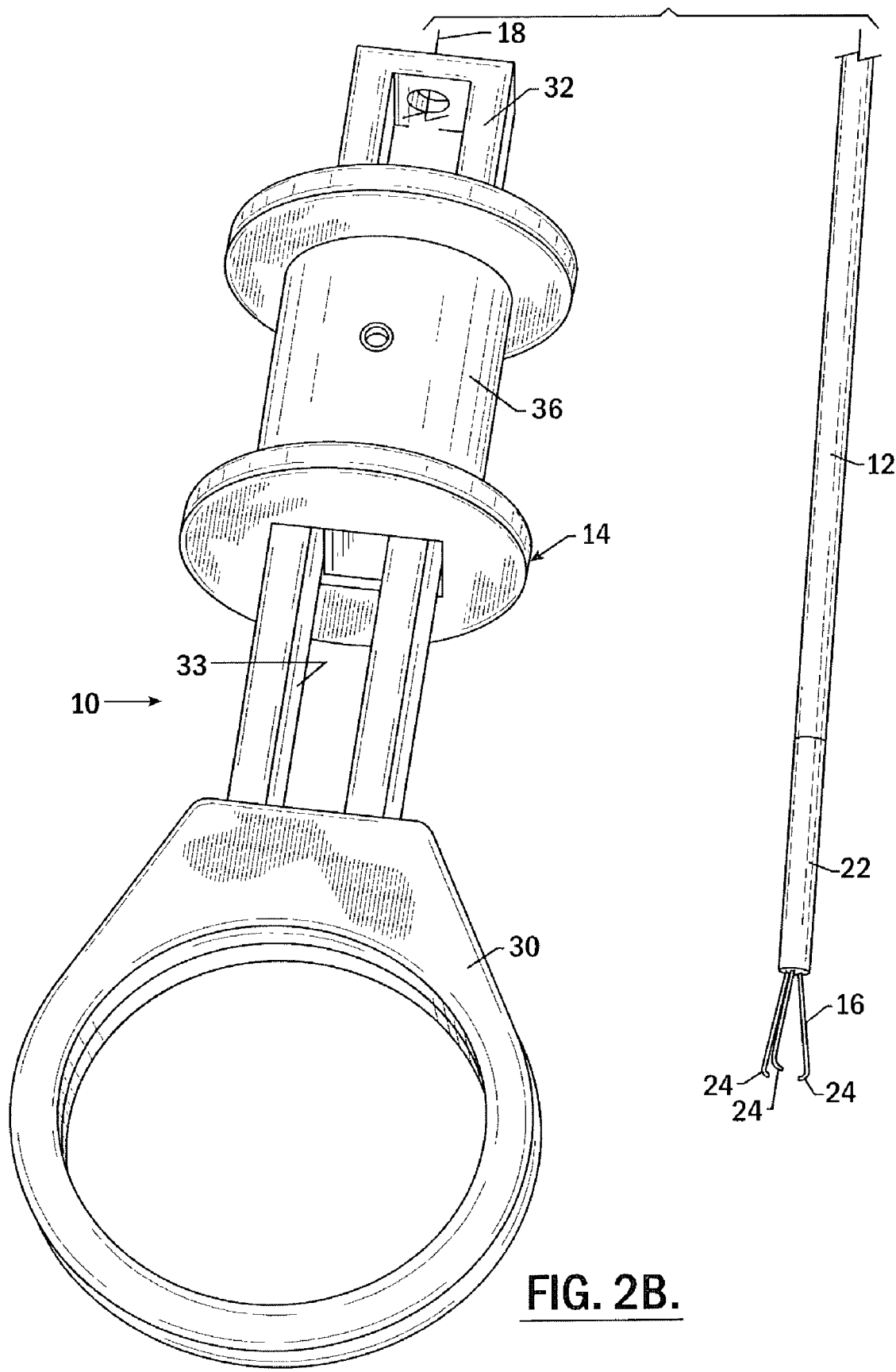
FIG. 2B is an enlarged perspective view similar to that of FIG. 2A, but showing the instrument's cam member and outer sleeve partially retracted to partially open the longitudinally fixed manipulation members.
Figure 2C:
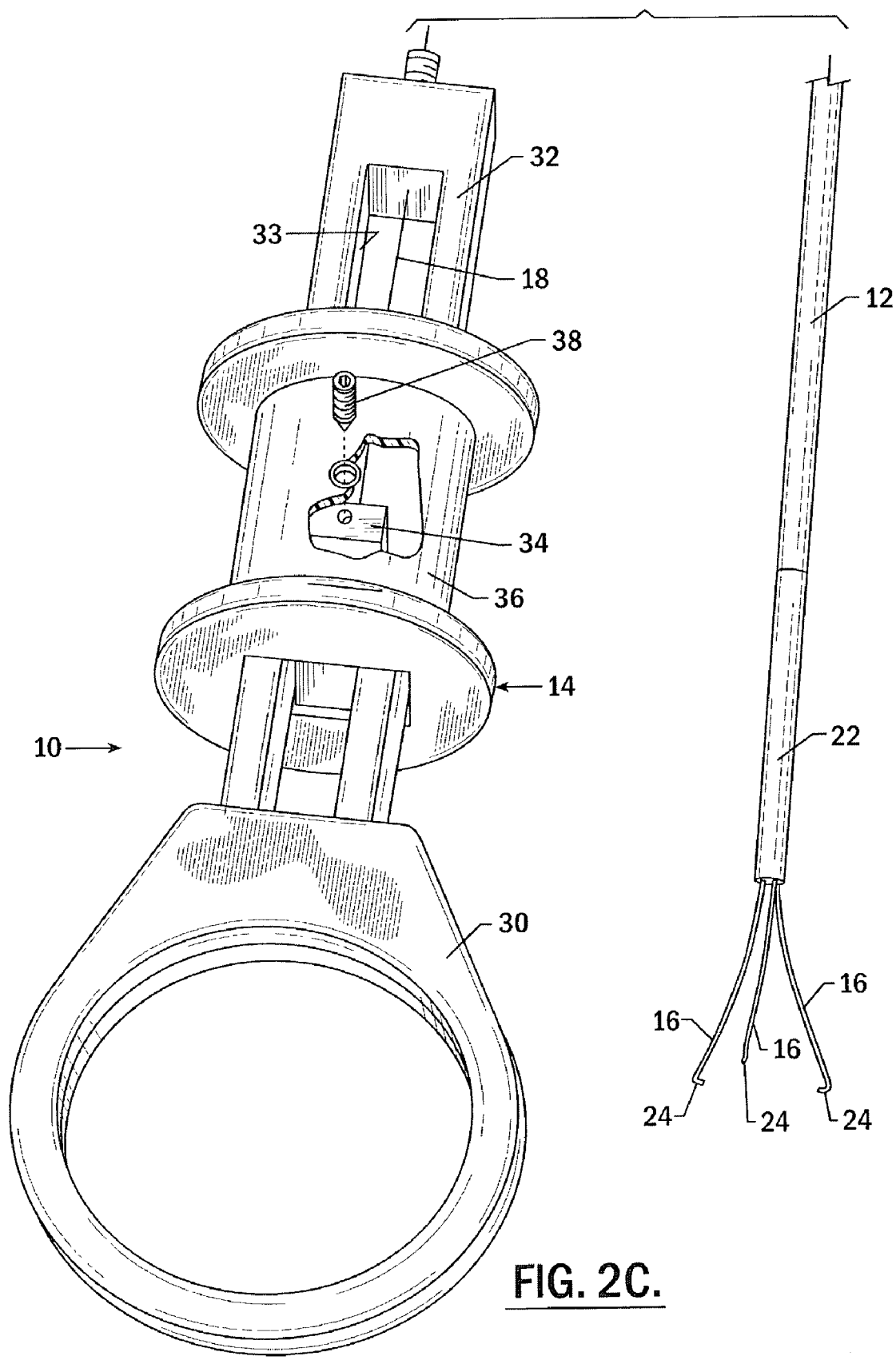
FIG. 2C is an enlarged perspective view similar to that of FIGS. 2A and 2B, but showing the instrument's cam member and outer sleeve fully retracted to fully open the longitudinally fixed manipulation members.
Figures 3A, 3B:
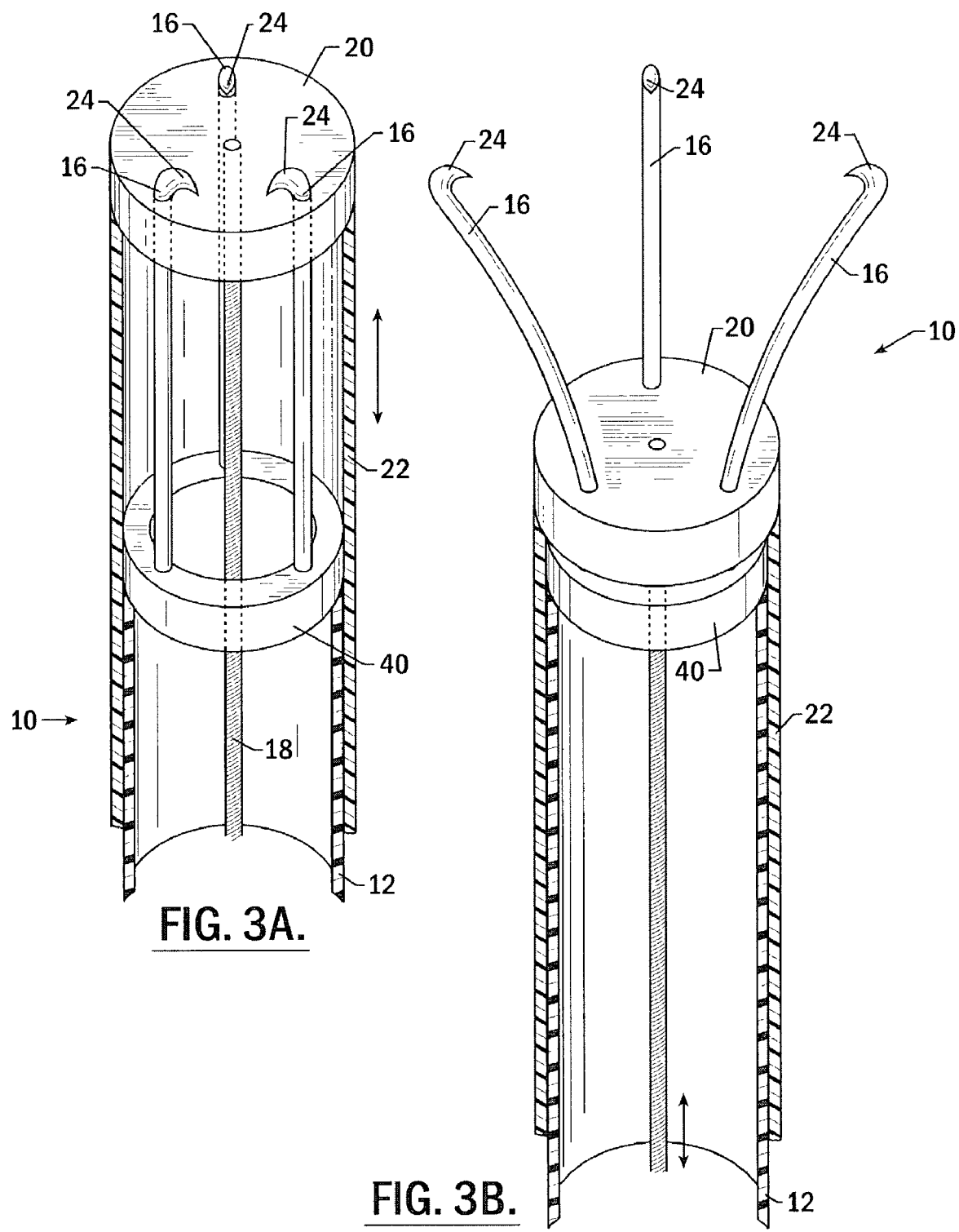
FIGS. 3A and 3B are detailed partial cross-sectional views of the distal end of the instrument of FIGS. 1 through 2C, showing the longitudinally fixed manipulation members in their open and closed conditions, respectively.

Because of this arrangement, as shown in FIGS. 2A through 2C, the jaws 16 are laterally supported and positively restrained by the cam member 20 throughout the entire closing operation, with such lateral support increasing as the jaws 16 are closed further, thus providing increased support as the jaws 16 grasp and grip an object. This allows the resilient or spring wire jaws 16 to be thinner, due to being laterally supported and thus effectively strengthened, and they are thus usable in tighter or narrower environments without sacrificing grasping or gripping strength. This arrangement also allows the jaws 16 to be formed with tighter curvatures, thus also allowing them to be shorter, with the resultantly lower length-to-diameter (L/D) ratio and increased column strength. The provision of the longitudinally movable cam member 20 deflecting the longitudinally fixed jaws 16 also allows for improved control of jaw motion, higher applied forces without undesirable changes or distortions in jaw shape or geometry while grasping an object. In addition, the jaws 16 are maintained in a constant location relative to the object to be manipulated and kept within the focal range of an endoscope.

The jaws 16 can optionally have hooked or barbed ends 24 or other discontinuities that aid in grasping, gripping, holding or otherwise manipulating an object. Furthermore, as shown in the preferred embodiments shown in the drawings, an outer sleeve 22 is preferably interconnected with the cam member 20 and movable therewith relative to the sheath 12 in order to resist the introduction of tissue or other materials into the sheath 12. In this regard, it is preferred that the outer sleeve 22 be long enough to slidably overlap the sheath 12 through out the entire range of retraction and extension of the cam member 20, as is illustrated in FIGS. 2A through 2C. It should also be noted that many of the advantages of the invention can also be had in other instruments that close the jaws upon retraction of the cam member rather than upon extension.

In FIGS. 4A and 4B, reference numerals similar to those of FIGS. 1 through 3B, except with one-hundred prefixes, are used to indicate elements that are similar to, or that correspond with, elements of FIGS. 1 through 3B. In FIGS. 4A and 4B, however, the multi-piece jaws 16 are replaced with an exemplary one-piece snare or loop 116. The loop 116 is forcibly closed and laterally supported and restrained by the extension of the cam member 120, as shown in FIG. 4A. Because the loop 116 is preferably resilient and biased toward its open condition, as shown in FIG. 4B, it opens upon retraction of the cam member 120. In most respects, however, as is the case with essentially all the exemplary embodiments shown in the drawings and discussed herein, the instrument 110 functions in a manner similar to that of the instrument 10 of FIGS. 1 through 3B, provides essentially the same advantages, and is susceptible to essentially the same alterations and variations as those discussed above in connection with FIGS. 1 through 3B.

Figures 5A, 5B:
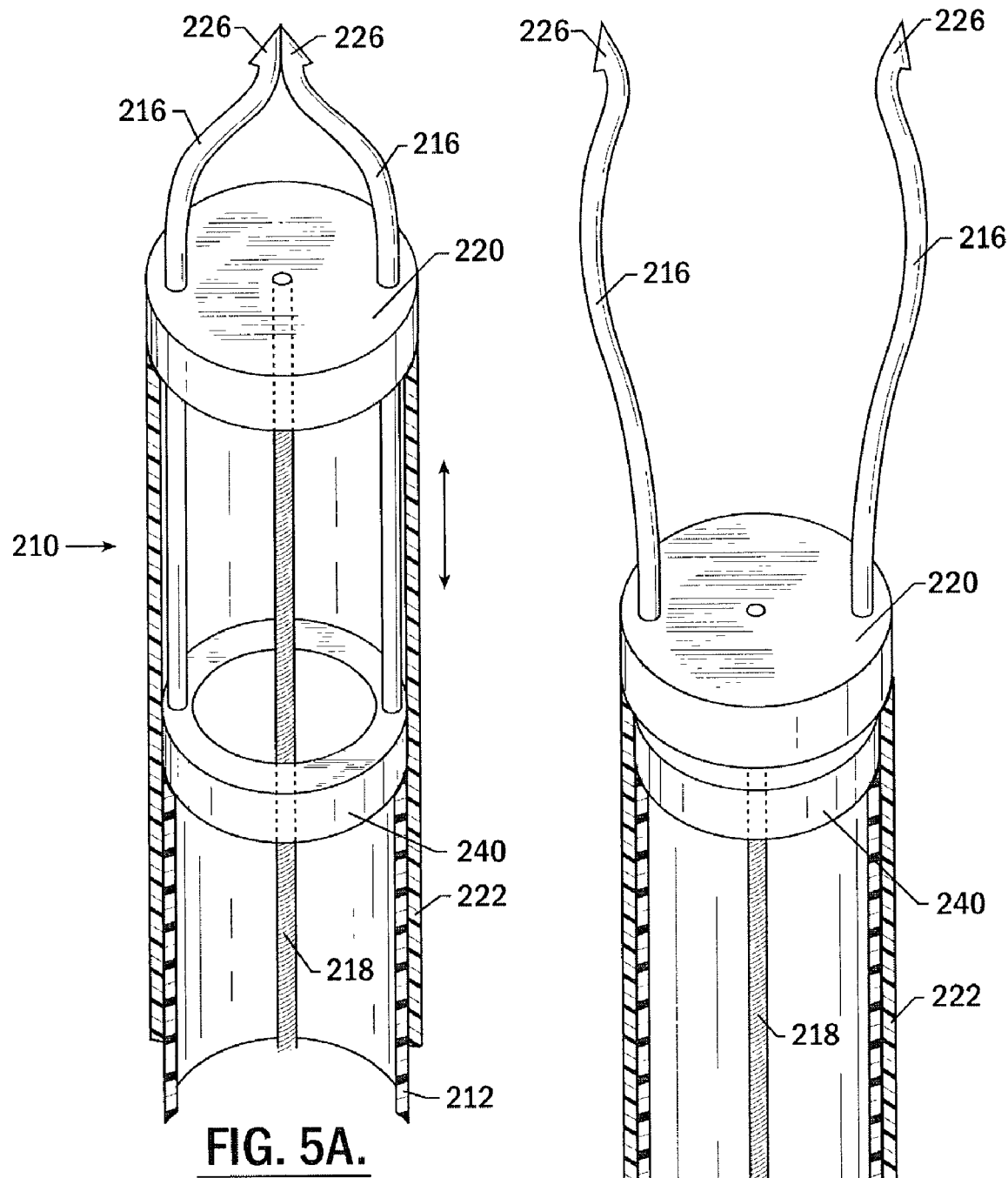
FIGS. 5A and 5B are detailed partial cross-sectional views similar to those of FIGS. 3A and 3B and those of FIGS. 4A and 4B, but illustrating another alternate embodiment of the longitudinally fixed manipulation members in their open and closed conditions, respectively.

As with those of FIGS. 4A and 4B, similar or corresponding elements of FIGS. 5A and 5B are indicated by similar or corresponding element reference numerals, but have two-hundred prefixes. In FIGS. 5A and 5B, the two-piece jaws 216 function essentially as do the jaws 16, except that the jaws 216 preferably include outwardly-facing barbs 226 at their distal ends. This configuration allows the instrument 210 to be especially advantageous as an impaction removal device. The object to be removed can thus be punctured by forcing the external barbs 226 into the object and gripped internally so it can be extracted in situations where access to the object's periphery is limited.

Figures 6, 7:
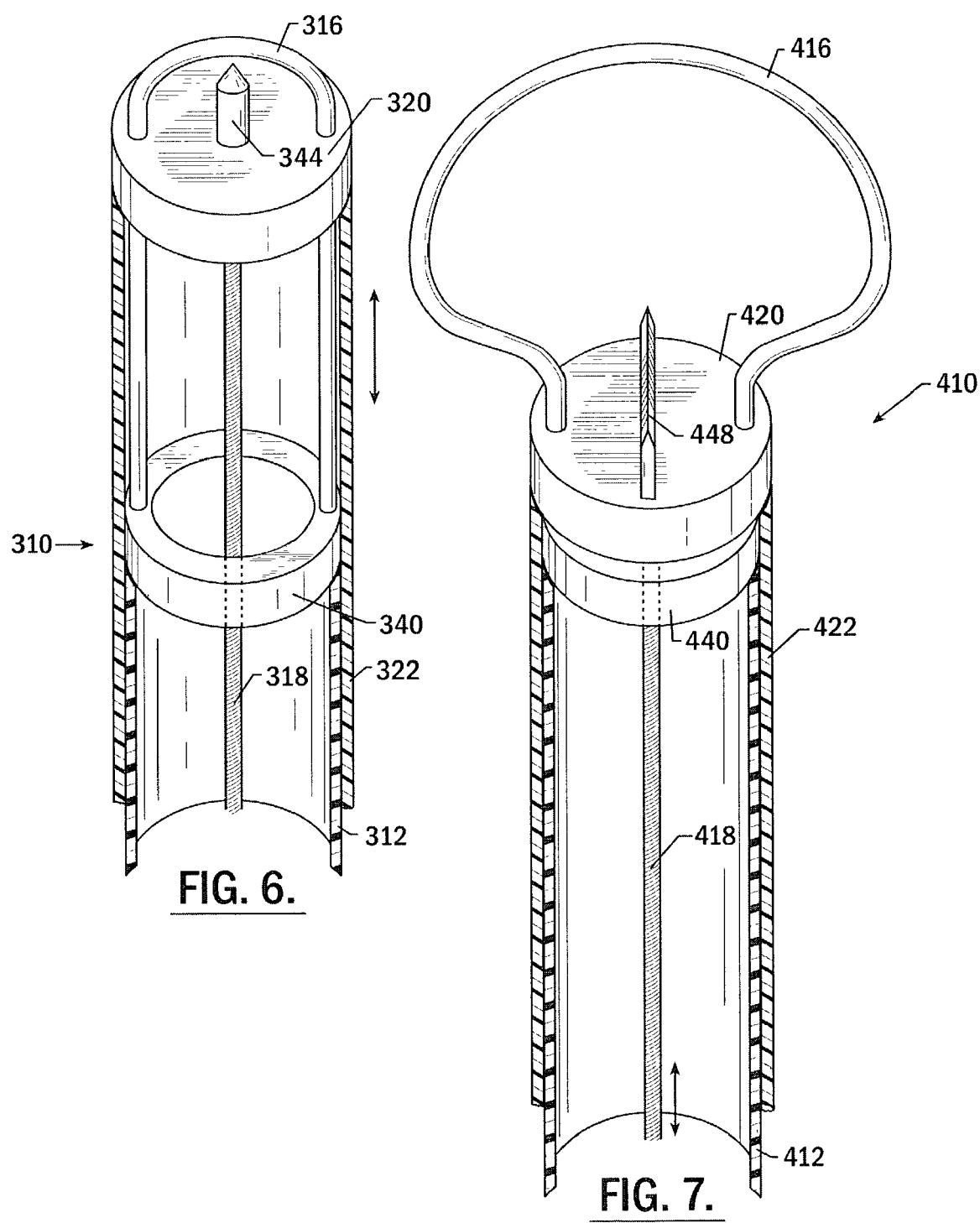
FIG. 6 is a detailed partial cross-sectional view of an instrument like that of FIGS. 4A and 4B, but including an exemplary secondary movable manipulation member in the form of a sharpened probe or needle mounted on the cam member.
FIG. 7 is a detailed partial cross-sectional views of an instrument like that of FIGS. 4A and 4B, but including an exemplary secondary movable manipulation member in the form of a knife or blade, mounted on the cam member.

FIGS. 6 and 7 include similarly corresponding element reference numerals to those of the preceding figures, but with three hundred and four hundred prefixes, respectively. In FIG. 6, a secondary or supplemental manipulation member in the form of the exemplary sharpened probe or needle 344 is mounted or otherwise interconnected with the cam member 320 for extension and retraction therewith in order to supplement or aid the snare or loop member 316. Similarly, in FIG. 7, the cam member 420 can have a knife, scalpel or other blade 448 movable therewith. It should be noted that other secondary or supplemental manipulation members can also be used and that any such secondary manipulation members can be advantageously used in conjunction with the other exemplary embodiments shown or suggested herein.

Figures 8A, 8B:
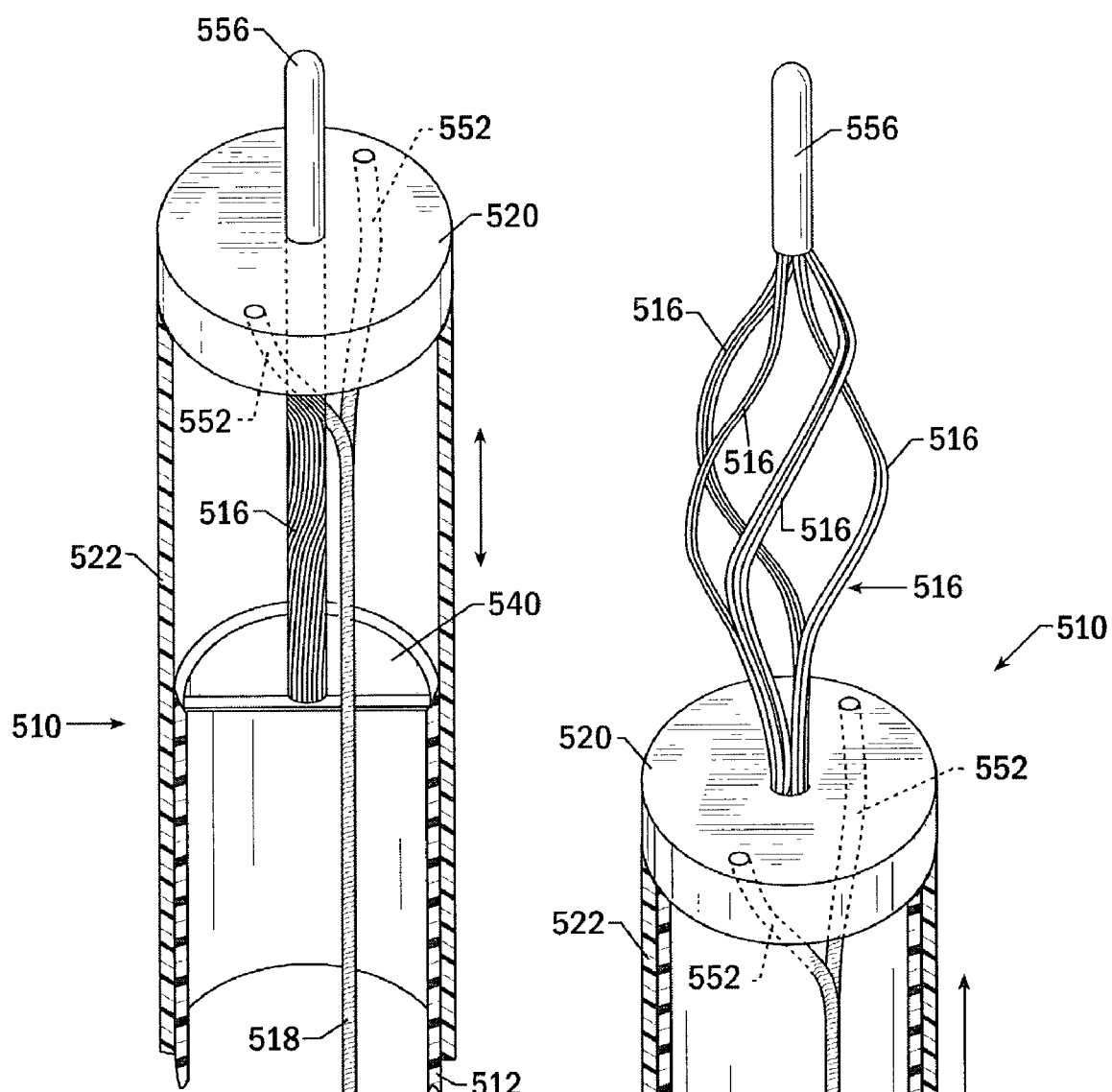
FIGS. 8A and 8B are detailed partial cross-sectional views similar to those of FIGS. 3A through 6, but illustrating another alternate embodiment having a laterally expandable and constrictable "basket-type" longitudinally fixed manipulation member assembly, shown in its open and closed conditions, respectively.

In FIGS. 8A and 8B, which also use similar or corresponding element reference numeral, but with five hundred prefixes, a "basket" type of jaw assembly construction or configuration is illustrated. Two or preferably more arcuate and spiraling wire-like jaw members 516 are laterally restrained relative to each other, preferably at both their proximate and distal ends. When the cam member 520 is retracted and extended, the basket-type jaw members 516 expand and constrict, respectively, in order to be maneuvered to surround or enclose and then grip or grasp the object to be manipulated. An outer cap or tip 556 is preferably included at the outer or distal end of the jaws 516 in order to protect the jaws 516 and to prevent them from snagging on, or causing damage to, the surface or wall of a body canal or other opening into which or through which the instrument 510 is inserted and used.

Furthermore, as shown in FIGS. 8A and 8B, the activation cable or wire 518 can include bifurcated end portions 552 that interconnect with the cam member 520 in a straddling relationship relative to the jaw assembly 516 extending generally through a central or medial area of the cam member 520.

Figure 9:
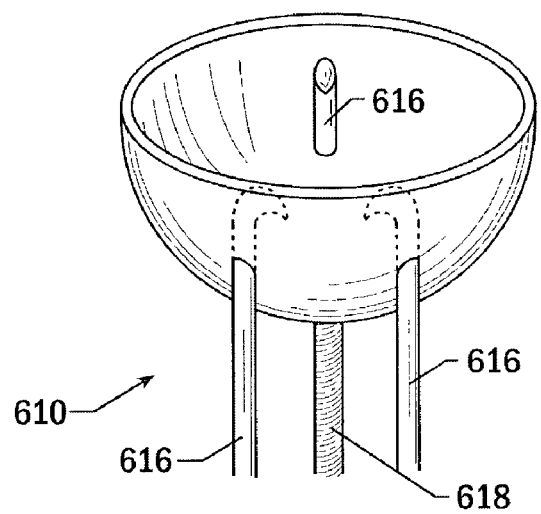
FIG. 9 illustrates an alternate cam member in its extended position, with the manipulation members in their closed condition and with their barbed outer ends within the generally cup-shaped outer portion of the cam member.

FIG. 9 illustrates an alternate construction for a cam member, which has an outwardly-opening cup-shaped or otherwise open end for surrounding and shielding the ends of the jaws 616, such as might be necessary or desired during insertion of the instrument wall into or through a body canal or other opening or lumen.

Figure 10A:
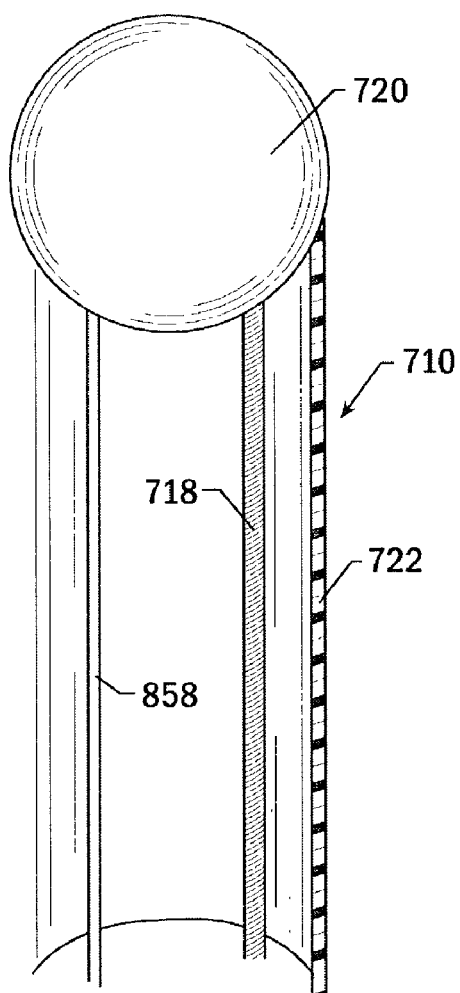
FIGS. 10A and 10B illustrate a generally spherical cam member, with an additional activation member attached to the cam member in order to allow the cam member to turn or steer the sheath portion of the instrument.
Figure 10B:
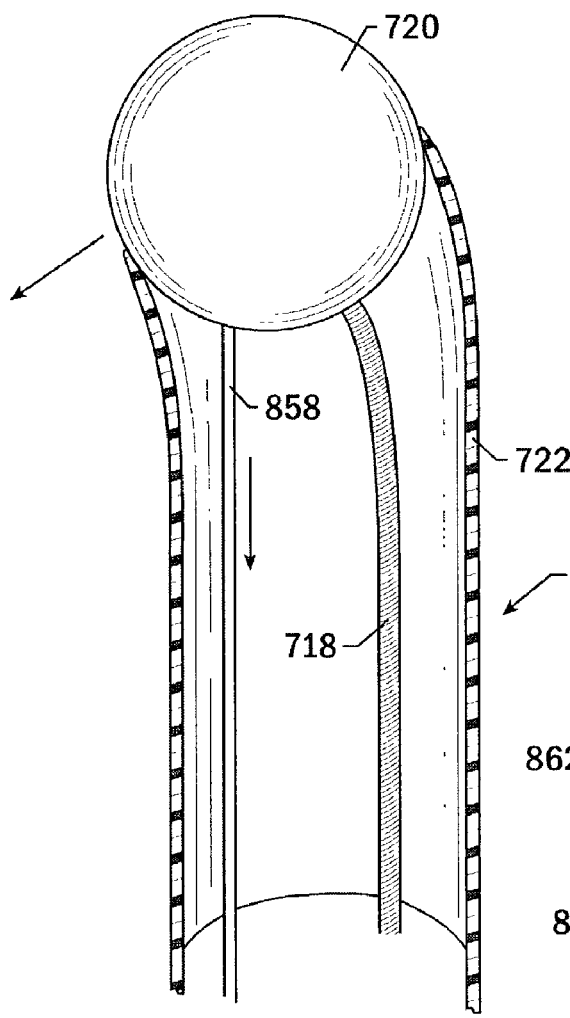
Figure 10C:
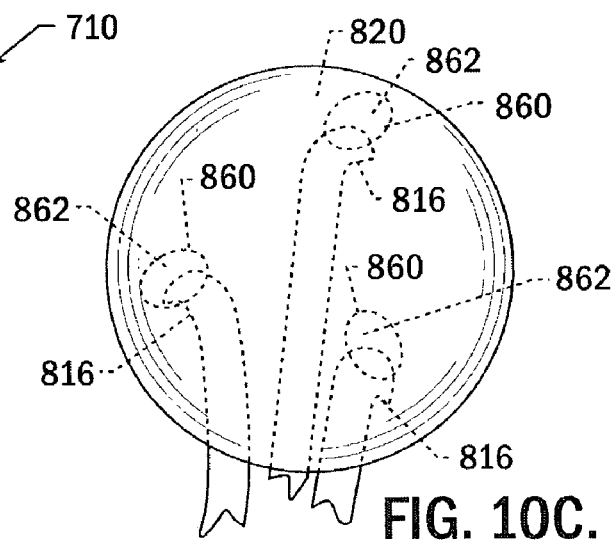
FIG. 10C illustrates a generally spherical cam member, similar to that of FIGS. 10A and 10B, but with optional recesses in its outer end, into which barbed ends of the manipulation members are received when the cam member is fully extended.

FIGS. 10A and 10B illustrate the optional use of one or more "steering" or turning cables or wires 858 that work along with the other activation cable or wire 718 to allow the generally spherical or "bead-like" cam member 720 to be more readily turned and maneuvered through a non-straight-line extending opening, canal or lumen. It should be noted that one or more of such turning cables can also be used in conjunction with the other embodiments of the invention shown or suggested herein.

As is schematically shown in FIG. 11C, a generally spherical cam member 820 (or cam members of other shapes) can also include outer recesses into which the barbed ends of the jaws 816 can be received to prevent them from snagging on or damaging the wall of an opening or canal.

Finally, in any of the exemplary arrangements or embodiments shown in the drawings and discussed or suggested herein, the individual single or multiple jaws or other manipulation members can have virtually any cross-sectional shape, such as round or other arcuate shapes, or even rectangular or other polygonal shapes, in order to suit a particular application or to obtain certain desired directional deflection characteristics.

Those skilled in the art will readily recognize that the present invention has broad utility and wide-ranging application. Alternate embodiments and adaptations of the present invention other than those shown and described herein, as well as variations, modifications and equivalent arrangements, will be apparent from! or reasonably suggested by the present invention, as described in the drawings, the foregoing description thereof, and the appended claims, without departing from the substance or scope of the present invention, as defined in the following claims.

What is claimed is:

1. An endoscopic instrument for manipulating an object, the instrument comprising:
    a generally hollow elongated sheath;
    a selectively operable handle assembly generally adjacent one end of said sheath;
    a plurality of manipulation members generally adjacent an opposite end of said sheath, said manipulation members being generally longitudinally fixed relative to said sheath and being at least partially deflectable in at least one lateral direction;
    an elongated activation cable extending generally longitudinally within said hollow sheath and being longitudinally moveable therein, said cable member further being interconnected with said handle assembly for selective longitudinal movement between a longitudinally retracted position relative to said sheath and a longitudinally extended position relative to said sheath in response to selective operation of said handle assembly; and
    a cam member fixed relative to said cable member for longitudinal movement therewith between said retracted and extended positions, said longitudinally moveable cam member engaging and forcibly deflecting said longitudinally fixed manipulation members laterally inwardly in response to movement of said cam member toward said extended position and laterally outwardly in response to movement of said cam member toward said retracted position in order to force said manipulation members into a gripping engagement with the object, said manipulation members remaining generally longitudinally fixed relative to said sheath during said non-longitudinal deflection, and said cam member has having a plurality of openings extending therethrough, each of said openings slidably receiving said at least a portion of one of said manipulation members extending therethrough during said longitudinal movement of said cam member.

2. An instrument according to claim 1, wherein said each of said manipulation members includes a discontinuity protruding laterally outwardly therefrom, said discontinuities being grippingly engageable with the object when said manipulation members are deflected laterally outwardly and forced into engagement with the object.

3. An instrument according to claim 1, wherein at least a portion of said manipulation member is resiliently and laterally deflectable.

4. An endoscopic instrument for manipulating an object, the instrument comprising:
    a generally hollow elongated sheath;
    a selectively operable handle assembly generally adjacent one end of said sheath;
    a generally loop-shaped manipulation member generally adjacent an opposite end of said sheath, said manipulation member being generally longitudinally fixed relative to said sheath and being at least partially deflectable in at least one lateral direction;
    an elongated activation cable extending generally longitudinally within said hollow sheath and being longitudinally moveable therein, said cable member further being interconnected with said handle assembly for selective longitudinal movement between a longitudinally retracted position relative to said sheath and a longitudinally extended position relative to said sheath in response to selective operation of said handle assembly; and
    a cam member fixed relative to said cable member for longitudinal movement therewith between said retracted and extended positions, said longitudinally moveable cam member engaging and forcibly deflecting said at least a portion of longitudinally fixed manipulation member laterally inwardly in response to movement of said cam member toward said extended position and laterally outwardly in response to movement of said cam member toward said retracted position in order to force said manipulation member into a gripping engagement with the object, said manipulation member remaining generally longitudinally fixed relative to said sheath during said non-longitudinal deflection and said cam member having a plurality of openings extending therethrough, each of said openings slidably receiving said at least a portion of one of said manipulation members extending therethrough during said longitudinal movement of said cam member.

5. An instrument according to claim 4, wherein at least a portion of said manipulation member is resiliently and laterally deflectable.

6. An instrument according to claim 4, further including at least a second manipulation member generally fixed with respect to said cam member and moveable therewith between an engaged position in contact with the object and a disengaged position out of contact with the object.

7. An instrument for manipulating an object, the instrument comprising:
    a generally hollow and flexible elongated sheath;
    a selectively operable operating assembly generally adjacent one end of said sheath;
    an elongated activation member extending generally longitudinally relative to said hollow sheath and being longitudinally moveable, said activation member being interconnected with said operating assembly for selective longitudinal movement between a longitudinally retracted position relative to said sheath and a longitudinally extended position relative to said sheath in response to selective operation of said operating assembly; and
    a cam member having a solid body portion formed with at least two opening extending longitudinally therethrough; and
    at least two relatively thin resilient wire members passing longitudinally through said openings in said cam member and being biased in a radial direction relative to said longitudinal extent of said elongated activation member, and said resilient wire members being slidably mounted in said openings in said cam member and moved relative to said cam by said movement of said activation member, with said resilient wire members being moved toward and away from one another for grasping and releasing objects by said relative movement between said resilient wire members and said cam member and wherein said cam member is fixed to said activation member for longitudinal movement therewith, and wherein said resilient wire members are fixed relative to said sheath, whereby said longitudinal movement of said activation member causes said relative movement between said resilient members and said cam.

8. An instrument according to claim 7, wherein said openings in said cam member have a configuration corresponding to the cross-sectional configuration of said resilient wire members.

9. An instrument according to claim 7, wherein said resilient wire members are biased radially outwardly relative to said longitudinal extent of said elongated activation member, and wherein said movement of said cam member relative to said resilient wire members moves said resilient wire toward one another and against said bias.

* * * * *